(12) United States Patent
Hussain et al.

(10) Patent No.: US 7,037,523 B2
(45) Date of Patent: May 2, 2006

(54) CONTROLLED RELEASE COMPOSITIONS FOR MACROLIDE ANTIMICROBIAL AGENTS

(75) Inventors: Javed Hussain, Maharashtra (IN); Pankaj Khapra, Maharashtra (IN); Arun S. Gosavi, Maharashtra (IN)

(73) Assignee: Wockhardt Limited, (IN)

( * ) Notice: Subject to any disclaimer, the term of this patent is extended or adjusted under 35 U.S.C. 154(b) by 0 days.

(21) Appl. No.: 10/286,389

(22) Filed: Nov. 1, 2002

(65) Prior Publication Data

US 2003/0119760 A1    Jun. 26, 2003

Related U.S. Application Data

(60) Provisional application No. 60/338,234, filed on Nov. 2, 2001.

(51) Int. Cl.
  *A61K 31/00* (2006.01)
  *A61F 2/00* (2006.01)
(52) U.S. Cl. ............... 424/468; 424/464; 424/480; 514/27; 514/28; 514/29; 514/30
(58) Field of Classification Search ............... 514/29, 514/57, 27, 28, 30; 424/464, 468, 480
See application file for complete search history.

(56) References Cited

U.S. PATENT DOCUMENTS

| | | | | |
|---|---|---|---|---|
| 3,843,787 A | * | 10/1974 | Fabrizio ............... 514/29 |
| 4,842,866 A | | 6/1989 | Horder et al. ............... 424/468 |
| 5,082,656 A | | 1/1992 | Hui et al. ............... 514/24 |
| 5,292,522 A | | 3/1994 | Petereit et al. ............... 424/490 |
| 5,419,917 A | | 5/1995 | Chen ............... 429/469 |
| 5,462,747 A | | 10/1995 | Radebaugh et al. ............... 424/465 |
| 5,478,573 A | | 12/1995 | Eichel ............... 424/480 |
| 5,695,781 A | | 12/1997 | Zhang et al. ............... 424/468 |
| 5,705,190 A | | 1/1998 | Broad et al. ............... 424/465 |
| 6,010,718 A | | 1/2000 | Al-Razzak et al. ............... 424/464 |

FOREIGN PATENT DOCUMENTS

| | | |
|---|---|---|
| EP | 1064942 | 1/2001 |
| JP | 0995440 | 4/1997 |
| WO | WO-00/48607 | 8/2000 |
| WO | WO-01/62229 | 8/2001 |
| WO | WO-02/241174 | 3/2002 |

OTHER PUBLICATIONS

Erah, P..O. ,et al. , "The Stability of Amoxycilin, Clarithromycin and Metronidazole in Gastric Juice: Revelance to the Treatment of *Helicobacter pylori* Infection", *Journal of Antimicrobial Chemotherapy,* vol. 39,(1997),pp. 5-12.

Ostberg, T..,et al. , "Calcium Alginate Matrices for Oral Multiple Unit Administration: IV. Release Characteristics in Different Media", *International Journal of Pharmaceutics,* vol. 112,(1994),pp. 241-248.

Salem, I..I. , *Analytical Profiles of Drug Substances and Excipients,* vol. 24, Academic Press,(1996),pp. 46-85.

Thombre, A..G. ,et al. , *Encyclopedia of Pharmaceutical Technology,* vol. 2,(1990),pp. 61-88.

* cited by examiner

*Primary Examiner*—Elli Peselev
(74) *Attorney, Agent, or Firm*—Schwegman, Lundberg, Woessner & Kluth, P.A.

(57) ABSTRACT

The present invention provides a controlled release pharmaceutical composition of an acid labile, poorly soluble drug having pH dependent solubility profile in aqueous environment. In a preferred embodiment the drug is combined with a practically water insoluble polymer an optimizing agent and optional additives to produce a controlled release of therapeutic agent when compositions is exposed to aqueous environment.

46 Claims, No Drawings

CONTROLLED RELEASE COMPOSITIONS FOR MACROLIDE ANTIMICROBIAL AGENTS

CROSS-REFERENCE TO RELATED APPLICATION

This application claims priority from U.S. Provisional Patent Application No. 60/338,234, filed Nov. 02, 2001, which application is incorporated herein by reference.

BACKGROUND OF INVENTION

Controlled drug delivery devices offer clinically significant advantages for various therapeutically active agents by way of increasing patient compliance due to reduced frequency of administration, improve the safety and efficacy of drug substances and reduce undesirable effects in comparison to the corresponding immediate release dosage form. The advantages of controlled release or sustained release or modified release products are well known in the pharmaceutical field.

Many such drug delivery devices are commercially available and are produced by various technologies known in the art. However, some of these technologies require special processes and equipment for production. In addition, some of these systems have limited applications because their ability to produce a desired release profile of a therapeutic agent depends upon several factors, e.g., the physico-chemical properties of therapeutic agent, additives in the drug delivery device, physiological factors and the like. The object of a controlled drug delivery device or composition is to limit, control or modify (e.g., slow) the drug release characteristics relative to an immediate release system of the same drug. While, many controlled release formulations are already known, certain moderately to poorly soluble or practically insoluble drugs present formulation difficulties and cannot be successfully formulated as a controlled drug delivery device employing these formulation techniques. In addition, due to variability in physico-chemical characteristics of the therapeutic agent, variation in their response in the body upon administration and variation in their response on combining with additives, some of the existing technologies are inadequate. The emergence of newer therapeutic agents and understanding of pharmacokinetics and physiological needs make the task of controlled drug delivery more complex.

Clarithromycin is a 14-membered macrolide antimicrobial agent that exhibits a broad spectrum of antimicrobial activity against gram-positive and gram-negative pathogens making it suitable for numerous clinical situations demanding antibacterial agents. Depending on the pharmacokinetic characteristics, antibacterial agents may be administered orally more than once per day to maintain a minimum effective concentration throughout the day and night. However, a more desirable dosage regimen is once a day administration. Currently, Clarithromycin is administered twice daily in the form of commercially available immediate release compositions. Clarithromycin is practically insoluble in water and shows pH dependent solubility profile. The solubility significantly increases at lower pH values (I. I. Salem, *Analytical Profiles of Drug Substances and Excipients*, Volume 24, Academic Press, (1996) at 46–85)

Clarithromycin undergoes degradation in acidic medium. It degrades rapidly at normal gastric pH of 1.0–2.0 (P. O. Erah et. al., *J. Antimicrob. Chemother.* 39, 5–12, (1997)). On the market, Clarithromycin is present in the form of film coated tablets, a suspension and extended-release tablets.

Various compositions with extended-release characteristics are known in the art for example, Horder et al. (U.S. Pat. No. 4,842,866), disclose a slow release composition comprising sodium alginate, sodium-calcium alginate and a therapeutically effective ingredient.

Broad et al. (U.S. Pat. No. 5,705,190) disclose a controlled release solid pharmaceutical compositions adopted for oral administration comprising a water soluble alginate salt, a complex salt of alginic acid, wherein the cation is selected from the group consisting of calcium, strontium, iron or barium, and an organic carboxylic acid to facilitate dissolution of basic drug. These formulations are said to be suitable for once a day administration. The release rate of the Clarithromycin is controlled using a matrix based on a water-soluble alginate salt and a complex salt of alginic acid.

The release model of a drug from calcium alginate matrices has been shown to be highly dependent on the release medium. Cross-linking calcium ions were rapidly discharged from the matrices in the presence of acid and affected the ability to provide delayed drug release. (Ostberg, T. et. al., *Int. J. Pharm.* 112, 241–248 (1994)). It appears that such interactions may lead to inconsistent and unpredictable drug release upon administration of alginate based controlled drug delivery devices.

Al-Razzak et al. (U.S. Pat. No. 6,010,718) disclose a pharmaceutical composition for extended release of an erythromycin derivative in a gastrointestinal environment. The composition includes an erythromycin derivative and a hydrophilic water-soluble polymer. The polymer is selected from group consisting of polyvinyl pyrrolidone, hydroxypropyl cellulose, hydroxypropylmethyl cellulose (HPMC), methyl cellulose, vinyl acetate/crotonic acid copolymers, methacrylic acid copolymers, maleic anhydride/methyl vinyl ether copolymers and derivatives and mixtures.

Compositions based on hydrophilic water-soluble polymers commonly exhibit an initial "burst effect" which causes a non-linear release rate of a drug. (See, e.g., U.S. Pat. No. 5,419,917.) Polymers such as hydroxypropylmethyl cellulose can be hydrated at low pH levels to form a viscous gel layer that controls drug release. During drug release, at high pH levels, however the tablets become smaller and smaller due to polymer erosion. The size reduction leads to a reduction in the surface area that may affect the dissolution rate. (See U.S. Pat. No. 5,695,781.)

The processing of these hydrophilic water-soluble polymers such as hydroxypropylmethyl cellulose, is difficult and requires strict controls. For example, Koji et al. (JP 09095440) disclose a lyophilized composition of a fluid mixture of medicine and hydrogel forming polymer (such as hydroxypropyl cellulose, and hydroxypropylmethyl cellulose). The Koji composition is said to float in the stomach and release a medicament slowly.

Gel forming cellulose ethers (e.g., hydroxypropyl cellulose and hydroxypropylmethyl cellulose) have been used in controlled release of drug delivery to preparing matrix systems. However, the mechanism of release from these matrices depends on the aqueous solubility of the drug and the hydrophilicity of the polymer used. (A. G. Thombre & J. R. Cardinal in Encyclopedia of Pharmaceutical Technology, Volume 2, 1990, 61–88).

Lek (WO 00/48607) discloses a formulation including Clarithromycin or a derivative and a mixture of fatty and hydrophilic components. The formulation also includes a surfactant and pH modulator, along with other pharmaceutically acceptable additives. An acid resistant coating on the tablet formulation has been disclosed.

Insoluble polymers such as ethyl cellulose (EC) have been used for controlling the release of therapeutic agents from drug delivery devices. For example, ethyl cellulose has been used extensively as a coating layer for dosage forms to control the release of a therapeutic agent. However, ethyl cellulose is insoluble at gastrointestinal pH. Therefore, the drug release depends upon the permeability of the EC films. The aqueous fluids penetrate and dissolve the drug, which can diffuse out from the dosage form. The rate of release is dependent upon the drug solubility in the gastrointestinal environment. Thus, the coatings may provide a formulation having a pH dependent release rate and variability in the release rate of drugs that are insoluble at gastrointestinal pH. Moreover, the coating process requires a controlled operation because a variation in the thickness of the coating on the composition can lead to variation in drug release.

Attempts have been made to incorporate ethyl cellulose in sustained release matrix. Radebaugh et al. (U.S. Pat. No. 5,462,747) disclose a process for preparing a composition of a pharmaceutically active agent for sustained release, in the form of shaped tablets or tablet layers, characterized by a long lasting slow and relatively regular incremental release of a the active agent upon administration. The composition includes a granulating agent such as povidone, a polymer such as ethyl cellulose, a wicking agent such as microcrystalline cellulose, erosion promoter such as pregelatinized starch to form a granulation. The granulation is then blended with a composition of an active agent an erosion promoter, wicking agent, lubricant, glidant before compressing into tablet. The goal of the '747 patent is said to be a long lasting and relatively regular incremental release of the pharmaceutically active agent upon administration. The release has been shown to be pH independent. The amount of EC is from 3–12 parts by weight of total non-active components of tablet. The pharmaceutically active agent is selected from various therapeutic categories.

Eichel et al. (U.S. Pat. No. 5,478,573) describe a delayed, sustained-release pharmaceutical preparation including a core of a drug such as propranolol hydrochloride surrounded by a hydrated diffusion barrier having thickness of at least 20 microns, comprising of film forming polymer mixture of an acrylic resin and ethyl cellulose. In one embodiment an acrylic resin such as Eudragit RS 30D and RL 30D are mentioned. The core drug is preferably a water-soluble drug. The thickness of the barrier layer is such that less than 5% of drug dissolves within 2 hours of administration.

Clarithromycin is very soluble in the stomach and fairly soluble in the upper region of small intestine where absorption is most likely to occur. As the drug's solubility decreases in the lower intestine, less drug is available for absorption. (See, e.g., U.S. Pat. No. 5,705,190.) Usually the time required for such type of composition to pass through distal end of small intestine is 6 to 8 hrs.

Thus, a continuing need exists for compositions capable of delivering therapeutic agents, such as, for example, Clarithromycin in at a rate sufficient to provide a beneficial effect, wherein the maximum delivery of the therapeutic agent will be within the 6–8 hour absorption window.

There is a need for a controlled drug delivery devices, such as, tablets, caplets, capsules, and the like, for delivery of therapeutic agents, which are capable of offering the advantages associated with a controlled drug delivery device while maintaining the desired bioavailability after administration.

In one aspect the invention provides a controlled release pharmaceutical compositions for an acid labile, poorly soluble therapeutic agent, exhibiting pH dependent solubility characteristics when exposed to aqueous environment.

In another aspect the present invention provides a controlled release composition and simple method for preparing a controlled release composition for macrolide antibacterial agents such as, for example, Clarithromycin salts and derivatives thereof.

In another aspect the present invention provides a convenient dosage form for Clarithromycin, a pharmaceutical salt or a derivative thereof that facilitates patient compliance.

Yet another aspect the present invention provides a process for making a controlled release compressed dosage form such as tablet, pill, or caplet of a therapeutic agent when present in a physical form is difficult to compress or has poor flow or results in said dosage forms having poor physical characteristics like friability or defects like capping or lamination which otherwise requires special equipments or excipients to produce said dosage forms. The therapeutic agent is selected from group comprising of macrolide group of antibacterial agents such as clarithromycin.

SUMMARY OF THE INVENTION

The present invention provides a controlled release pharmaceutical composition that includes a therapeutic agent having poor solubility in aqueous environment such as, for example, a macrolide antibacterial. The composition includes a mixture of the therapeutic agent, a water insoluble polymer, and an optimizing agent. In addition, the composition can also include fillers, binders, and other additives. The invention also provides a process for converting a therapeutic agent, having poor tableting characteristics, into a controlled release solid dosage form.

Often the formation of dosage forms such as tablets having therapeutic agents present in a physical form having poor tableting characteristics results in and/or otherwise requires special equipment, processes or excipients. According to the process of the invention, the therapeutic agent is converted to a dosage form having optimum characteristics and can be readily employed for the compositions of the invention.

DETAILED DESCRIPTION OF THE INVENTION

In the context of the present invention a number of terms have been used. In order to provide a clear and consistent understanding of the specification, claims and the scope, the following definitions are provided. Where specifically not indicated the terms used herein are used according to their normal and or art recognized meaning.

"Controlled release" as used herein, means sustained release or slow release or modified release or prolonged release or extended release or other similar terms used to indicate a composition providing an extended profile of drug release from the composition when exposed to aqueous environment either in-vitro or in-vivo as compared to an immediate release composition.

"Poorly soluble or poor solubility" as used herein, has the same meaning as is described in U.S. Pharmacopoeia XXIV and is used interchangeably with slightly soluble. Typically, a slightly soluble compound has a solubility of about 1 part in from about 100 to about 1000 parts of solvent, e.g., water. (Further, a saturated solution of a slightly soluble compound in water can have a concentration of from about 1 mM to about 100 mM of the compound or a saturated solution and an insoluble of a compound in water can have a concentration of less than about 1 mM.)

"Acid susceptible compounds" as used herein, refers to compounds or active agents that degrade when allowed to contact an acidic environment such as acidic gastric juices.

"Therapeutic agent, active agent or drug" as used herein, have been used interchangeably and have the meanings recognized by one skilled in the art.

The therapeutic agent is a macrolide antibacterial agent. Specific macrolide antibacterial agents include compounds such as, for example, clarithromycin, erythromycin, azithromycin, dirithromycin, roxithromycin, derivatives thereof and pharmaceutically acceptable salts thereof. Preferably the macrolide antibacterial agent is clarithromycin, derivatives thereof or a pharmaceutically acceptable salt thereof.

Examples of pharmaceutically acceptable salts are organic acid addition salts formed with acids, which form a physiological acceptable anion, for example, tosylate, methanesulfonate, malate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The amount of clarithromycin in the composition can vary from about 30% to about 75% by weight of the composition. Preferably the composition comprises about 40 to about 65% by weight of the clarithromycin salt or derivative. Most preferably the therapeutic agent comprises about 45 to about 60% of the clarithromycin salt or derivative.

The insoluble polymers useful in the invention are pharmaceutically acceptable polymers, such as, for example, water insoluble cellulosic derivatives, polyvinyl chloride, amino alkyl methacrylates and the like. Suitable water insoluble cellulose derivatives include polymers such as, for example, ethyl cellulose having a viscosity grade 7 cps, ethyl cellulose having a viscosity grade 10 cps, ethyl cellulose having a viscosity grade 20 cps, ethyl cellulose having a viscosity grade 100 cps.

Commercially available examples of ethyl cellulose compositions include products such as, for example, Surelease™, Aquacoat™ and mixtures thereof. Examples of such commercially available ethyl cellulose grades are Ethocel 7 cps, Ethocel 10 cps, Ethocel 20 cps and Ethocel 100 cps from Dow, Ltd. USA. Preferably the ethyl cellulose polymer is ethyl cellulose 7 cps and ethyl cellulose 10 cps. The most preferred ethyl cellulose polymer is ethyl cellulose 7 cps or a mixture of ethyl cellulose 7 cps and ethyl cellulose 10 cps.

The amount of the insoluble polymer in the composition is at least about 5% based on the total weight of the therapeutic agent present in the composition. Preferably, the insoluble polymer is from about 10 to about 40%. More preferably, the amount of polymer is from about 15% to about 35% of the amount of the therapeutic agent present in the composition. Most preferably, the amount of polymer is from about 20% to about 30% of the amount of therapeutic agent present in the composition.

The viscosity grade and amount of polymer present in composition can affect the release profile of the drug from the composition. Depending upon the desired drug release profile and drug characteristics, a mixture of one or more viscosity grades of polymer may be employed. Thus, adjustments with respect to polymer present in the composition may be made and are within the scope of the present invention.

The composition of the invention further comprises additives that can be used to modify the desired release profile of the therapeutic agent in the composition or the invention.

The present invention overcomes the problem of forming tablets with therapeutic agents that have poor tableting characteristics by incorporating an "optimizing agent" in the composition. Optimizing agents useful in practicing the present invention are lactose, dicalcium phosphate, calcium phosphate and polymethacrylates such as anionic polymers of methacrylic acid and methacrylate esters, cationic polymer with dimethyl aminoethyl ammonium functional group and mixtures thereof. Examples of suitable polymethacrylates such as anionic polymers of methacrylic acid and methacrylate esters, are disclosed in U.S. Pat. No. 5,292,522 ("the '522 patent"). The '522 patent discloses polymers comprising acrylic acid, methacrylic acid, alkyl esters of these acids and amino alkyl esters of these acids. These copolymers are commercially available from Rohm Pharma Gmbh under the tradename Eudragit®. Preferably the "optimizing agent" is a combination comprising a polymer of methacrylic acid and methyl methacrylate and a compound selected from the group consisting of lactose, dicalcium phosphate and tricalcium phosphate or a mixture thereof.

Preferably the composition comprises from about 10 to about 90% of the optimizing agent relative to the amount of therapeutic agent of the invention. More preferred are compositions wherein the "optimizing agent" is present from about 20 to about 60% of optimizing agent relative to the amount of therapeutic agent in the composition.

The compositions of the invention further comprise an optional binding agent. The preferred binding agents suitable for practicing the invention are low viscosity water soluble cellulose derivatives such as hydroxypropyl cellulose, hydroxypropylmethyl cellulose (HPMC), hydroxyethyl cellulose, sodium carboxy-methyl cellulose, alginic acid derivatives, polyvinyl pyrrolidone (PVP), soluble starches or mixtures thereof. A preferred binding agent is HPMC, PVP or mixtures thereof. Preferably the binding agent comprises from about 1 to about 10%. Preferably, the binding agent is from about 1 to about 4% by weight of the composition.

In addition to the above ingredients, the compositions of the invention may further comprise fillers such as microcrystalline cellulose, mannitol, sorbitol, starches and the like, including mixtures thereof as are well known in the art. Preferably fillers are present in an amount of from 0% to about 50% by weight, either alone or in combination. More preferably they are present from about 5% to about 20% of the weight of the composition.

However, the amount of fillers can be adjusted in order to render the composition suitable for converting into a pharmaceutical dosage form without affecting the efficacy of the compositions of the invention. The compositions, when presented in the form of a solid dosage form may further comprise additives like lubricants, glidants, antiadherents such as stearates, stearic acid, talc, silicon dioxide and mixtures thereof. When present these additives comprise from 0 to about 5% by weight either alone or in combination.

Optionally the composition may further comprise additives known in the art such as, buffering agents such as, for example, citrates, carbonates, and the like; or surface active agents such as, for example, polysorbates, poloxamers and the like.

The additives included in the compositions of the invention may be added in amounts that are required to produce desired function of additive in order to administer the composition in the form of dosage form as are known in the art. The amounts and types of additives useful in the compositions of the invention are well known to those skilled in the art.

The compositions can be administered orally in the commonly known dosage forms in the art. The tablets, caplets, or pills suitable for oral administration can be prepared using standard tableting machines known in the art, which have appropriately sized dies. Compressed or molded solid dosage forms such as tablets, caplets, and pills are preferred. However, for the purpose of the present invention, any dosage forms suitable for administration of the composition of the invention, e.g., capsules and the like, are within the scope of the invention.

In other aspect of the invention provides a process for making an extended release composition by granulating and compressing a therapeutic agent, wherein the agent has a physical form that is poorly compressible, or other difficulties in compression. Some of the difficulties include tablets, etc., which have poor characteristics, such as capping, lamination, and/or high friability when compressed. According to the process of the invention, the therapeutic agent is mixed with a water insoluble polymer, and an optimizing agent as described herein.

The mixing of the ingredients is achieved with blenders (or mixers) that are commonly used in the pharmaceutical art such as, for example, a cone blender. The other additives, such as fillers or optional additives are added to the mixture prior to a final mixing. The order of addition of additives is not critical to the invention. Further, the process involves making granules of the mixture, prepared as described above, with a binding agent such as those described herein. According to the process the most preferred solvent for the binding agent is water. However, any other pharmaceutically acceptable solvent may be employed.

The blend may be granulated using methods that are known in the art, such as high shear or low shear granulators, mixers, and fluid bed granulators. The wet granules are ultimately dried, suitably sized by the techniques that are known in the art. The granules are blended with optional additives such as lubricants, glidants, antiadherents that are known in the art. Most preferably the additives are selected from group comprising of stearic acid or stearates, talc, silicon dioxide either alone or in combination. The final blend is then converted into tablets or a suitable solid dosage form by employing equipment such as tableting machines, which are known in the art.

Optionally the composition may be coated by film forming polymers and methods as are known in the art without significantly altering the objects of the inventions.

The following examples are intended to illustrate the invention without limiting the scope of the invention:

EXAMPLE 1

Preparation of Formulation & Drug Release Data

Ingredient Nos. 1 to 5 were blended. Purified water was added to granulate the blend. The granules were dried in a tray dryer at 60±2° C. The dried granules were then passed through 20 mesh sieve. The granules were then blended with ingredient no. 7, 8, and 9. Finally they were compressed into tablets. The resultant tablets could be readily compressed and had the desired physical characteristics. A single formulation was prepared according to the general method described above. The composition of the formulation is provided in Table 1.

TABLE I

| No. | Ingredient name | % w/w** |
|---|---|---|
| 1. | Clarithromycin [d(0.5) = 37.7 μm] | 57.3 |
| 2. | Ethyl cellulose 7 cps | 14.3 |
| 3. | Dicalcium phosphate | 17.2 |
| 4. | Eudragit L-100-55 | 5.7 |
| 5. | Hydroxypropyl cellulose | 2.9 |
| 6. | Magnesium stearate | 1.0 |
| 7. | Talc | 1.0 |
| 8. | Colloidal silicon dioxide | 0.6 |
| 9. | Purified water* | q.s. |

*Evaporates during processing.
**Values rounded off.

In-vitro dissolution studies were carried out using a buffered media of pH 5.0. Using USP Type II apparatus. The percent drug released is shown in Table II.

TABLE II

| Time (Hours) | % Drug Released pH 5.0 |
|---|---|
| 1 | 13.3 |
| 2 | 22.4 |
| 3 | 30.5 |
| 4 | 37.8 |
| 6 | 52.0 |
| 8 | 66.0 |

EXAMPLE 2

Preparation of Formulation & Drug Release Data

Ingredients 2 to 5 were blended in a cone blender. Resultant mixture was blended with ingredient no. 1. The blend obtained was granulated with aqueous dispersion of Kollidon K-30 in a low shear mixer. The granules obtained were dried until the loss on drying was less than 1.0%. The granules were blended with ingredient no. 7, 8, & 9 before compressing into caplets. The composition of the formulation is provided in Table III.

TABLE III

| No. | Ingredient name | % w/w** |
|---|---|---|
| 1. | Clarithromycin (<180 μm] | 57.3 |
| 2. | Ethyl cellulose 7 cps and Ethyl cellulose 10 cps (8:2) | 14.3 |
| 3. | Dicalcium phosphate | 13.7 |
| 4. | Lactose | 3.4 |
| 5. | Eudragit L-100-55 | 5.7 |
| 6. | Kollidon K-30 (10% aqueous dispersion) | 2.9 |
| 7. | Magnesium stearate | 1.0 |
| 8. | Talc | 1.0 |
| 9. | Colloidal silicon dioxide | 0.6 |

**Values rounded off.

Dissolution profile was studied in buffered medium of pH 5.0. The percent drug released is shown in Table IV.

TABLE IV

| Time (Hours) | % Drug Released pH 5.0 |
|---|---|
| 1 | 13.1 |
| 2 | 21.5 |
| 3 | 29.5 |
| 4 | 36.0 |
| 6 | 48.8 |
| 8 | 60.8 |
| 10 | 71.6 |
| 12 | 81.3 |
| 14 | 90.2 |

The finished composition, in the form of tablets or caplets, was evaluated for their physical parameters. The tablets did not show sign of unwarranted compression defects, had friability values in the range of 0.05 to 0.5% by weight. The caplets or tablets had acceptable appearance without the need for extraneous coatings.

EXAMPLE 3

Bioequivalence Study

Another composition was by prepared using the ingredients listed in Table V. Ingredients 1 to 4 were mixed in fluidized bed drier. The mixture was granulated with aqueous dispersion of ingredient 5 in fluidized bed drier. The granules were dried until the loss on drying was less than 2.0%.The dried granules were blended with ingredients 6,7 and 8 and compressed into tablets. The tablets were coated with an aqueous dispersion of ingredient 9.

The tablets were used in a controlled two way crossover bioequivalence study and compared to Biaxin® XL (Abbott Laboratories, USA), reference product. The ratio for LN Cmax and LN $AUC_{0-inf}$ was found to be in compliance with the requirement. The ratio of LN Cmax was 0.96 and the ratio of LN $AUC_{0-inf}$ was 1.00.

TABLE V

| No. | Ingredient Name | % w/w |
|---|---|---|
| 1 | Clarithromycin | 59.74 |
| 2 | Ethyl cellulose, 7 cps | 9.56 |
| 3 | Dicalcium phosphate | 17.92 |
| 4 | Methacrylic acid copolymer | 5.97 |
| 5 | PVP K-30 | 4.48 |
| 6 | Magnesium stearate | 0.72 |
| 7 | Talc | 1.02 |
| 8 | Colloidal silicon dioxide | 0.60 |
| 9 | Opadry Y-1-7000 | 20 mg/Tab |

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A pharmaceutical composition for controlled release of an active agent having antibiotic activity comprising a mixture of a macrolide antibacterial agent, a pharmaceutically acceptable water insoluble polymer and an optimizing agent.

2. The composition of claim 1, wherein the macrolide antibacterial agent is clarithromycin, erythromycin, azithromycin, dirithromycin, roxithromycin, a derivative or a pharmaceutically acceptable salt thereof.

3. The composition of claim 2, wherein the macrolide antibacterial agent is clarithromycin.

4. The composition of claim 1, further comprising a binder.

5. The composition of claim 1, wherein the particle size of the macrolide antibacterial agent is less than 180 μm.

6. The composition of claim 1, wherein the water insoluble polymer is a water insoluble cellulose derivative.

7. The composition of claim 6, wherein the cellulose derivative is ethyl cellulose.

8. The composition of claim 7, wherein the ethyl cellulose has a viscosity grade of 7 cps, 10 cps, 20 cps or 100 cps or mixtures thereof.

9. The composition of claim 8, wherein the ethyl cellulose has a viscosity grade of 7 cps or 10 cps.

10. The composition of claim 9, wherein the ethyl cellulose is a mixture of ethyl cellulose having a viscosity grade of 7 cps and 10 cps.

11. The composition of claim 1, wherein the amount of water insoluble polymer is at least about 5% by weight.

12. The composition of claim 1, wherein the amount of insoluble polymer is from about 10 to about 40%.

13. The composition of claim 12, wherein the amount of insoluble polymer is from about 15% to about 35%.

14. The composition of claim 13, wherein the amount of insoluble polymer is from about 20% to about 30%.

15. The composition of claim 1, wherein the optimizing agent comprises a polymer of methacrylic acid, methacrylate ester or a mixture thereof.

16. The composition of claim 15, wherein the optimizing agent comprises a co-polymer of methacrylic acid and a methacrylate ester.

17. The composition of claim 16, wherein the optimizing agent further comprises an additive; wherein the additive is lactose, dicalcium phosphate and tricalcium phosphate or a mixture thereof.

18. The composition of claim 17, wherein the additive comprises dicalcium phosphate.

19. The composition of claim 4, wherein the binder is a water soluble cellulose derivative, polyvinyl pyrrolidone or mixture thereof.

20. The composition of claim 19, wherein the binder comprises polyvinyl pyrrolidone.

21. The composition of claim 1, wherein the composition is a solid oral dosage form.

22. The composition of claim 21, wherein the dosage form is a tablet, pill, caplet, pellet or granule.

23. The composition of claim 22, wherein the dosage form is a capsule comprising pellets or granules.

24. The composition of claim 21, wherein the dosage form comprises a coating.

25. A process for preparing a pharmaceutical composition of claim 1, comprising mixing a macrolide antibacterial therapeutic agent, with a pharmaceutically acceptable water insoluble polymer and an optimizing agent.

26. The process of claim 25, wherein the macrolide antibacterial agent is selected from the group consisting of clarithromycin, erythromycin, azithromycin, dirithromycin, roxithromycin, derivative or a pharmaceutically acceptable salt thereof.

27. The process of claim 26, wherein the macrolide antibacterial agent the macrolide antibacterial agent is clarithromycin.

28. The process of claim 25, wherein the composition further comprises a binder.

29. The process of claim 28, wherein the binder is a water soluble cellulose derivative, polyvinyl pyrrolidone or mixture thereof.

30. The process of claim 25, wherein the particle size of the therapeutic agent is less than 180 μm.

31. The process of claim 25, wherein the wherein the water insoluble polymer is a water insoluble cellulose derivative.

32. The process of claim 31, wherein the cellulose derivative is ethyl cellulose.

33. The process of claim 32, wherein the ethyl cellulose has a viscosity grade of 7 cps, 10 cps, 20 cps or 100 cps or mixtures thereof.

34. The process of claim 33, wherein the ethyl cellulose has a viscosity grade of 7 cps or 10 cps.

35. The process of claim 34, wherein the ethyl cellulose is a mixture of ethyl cellulose having a viscosity grade of 7 cps and 10 cps.

36. The process of claim 25, wherein the amount of water insoluble polymer is at least about 5% by weight.

37. The process of claim 36, wherein the amount of insoluble polymer is from about 10 to about 40%.

38. The process of claim 37, wherein the amount of insoluble polymer is from about 15% to about 35%.

39. The process of claim 38, wherein the amount of insoluble polymer is from about 20% to about 30%.

40. The process of claim 25, wherein the optimizing agent comprises a polymer of methacrylic acid, polymethacrylates or a mixture thereof.

41. The process of claim 40, wherein the optimizing agent further comprises an additive; wherein the additive is lactose, dicalcium phosphate and tricalcium phosphate or a mixture thereof.

42. The process of claim 41, wherein the additive comprises dicalcium phosphate.

43. The process of claim 25, wherein the composition is a solid oral dosage form.

44. The process of claim 43, wherein the dosage form is a tablet, pill, caplet, pellet or granule.

45. The process of claim 25, wherein the therapeutic agent, and water insoluble polymer are blended by wet granulation.

46. The composition of claim 1, wherein the macrolide antibacterial agent is poorly soluble.

* * * * *